(12) United States Patent
Anderson

(10) Patent No.: US 7,054,768 B2
(45) Date of Patent: May 30, 2006

(54) METHOD AND SYSTEM FOR SHEAR FLOW PROFILING

(75) Inventor: Erik J. Anderson, Cambridge, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 26 days.

(21) Appl. No.: 10/875,051

(22) Filed: Jun. 22, 2004

(65) Prior Publication Data

US 2005/0283323 A1    Dec. 22, 2005

(51) Int. Cl.
*G01F 17/00*    (2006.01)

(52) U.S. Cl. ............................ 702/50; 405/52; 382/107

(58) Field of Classification Search ................. 702/50; 405/79, 52, 80; 472/128; 382/107
See application file for complete search history.

(56) References Cited

U.S. PATENT DOCUMENTS

| 6,336,771 B1 * | 1/2002 | Hill ............................. 405/79 |
| 2005/0018882 A1 * | 1/2005 | Muste et al. ................ 382/107 |

OTHER PUBLICATIONS

Anderson, E.J. et al. The Boundary Layer of Swimming Fish. Journal of Experimental Biology. 204, 81-102 (2001).
Hatem, A.B. et al. Improved Histogram Based Methods for PIV Vector Extraction. IMechE Conference Transaction, C516.043/06, Mar. 1996, pp. 259-265 (1996).
Mercer, C.R., ed. Optical Metrology for Fluids, Combustion and Solids. Ch. 3, Digital Particle Image Velocimetry, by Mark P. Wernet. pp. 69-104 (2003).
Stanislas, M. et al. (eds.) Particle Image Velocimetry. 279-290, 303-304 (2000).
Wernet, Mark P. Fuzzy interference enhanced information recovery from digital PIV using cross-correlation combined with particle tracking. Optical Techniques in Fluid, Thermal, and Combustion Flow, S. Cha, eds. Proc. SPIE 2456, 54-60 (1995).
Wernet, Mark P. Fuzzy logic particle tracking velocimetry. Optical Diagnostics in Fluid and Thermal Flow, S. Cha, eds. Proc. SPIE 2005, 701-8 (1993).

(Continued)

*Primary Examiner*—John Barlow
*Assistant Examiner*—Hien Vo
(74) *Attorney, Agent, or Firm*—Fish & Neave IP Group Ropes & Gray LLP

(57) ABSTRACT

The invention relates to a computerized method of profiling a shear flow, such as a boundary layer. The method includes receiving two successive images of a plurality of particles in the shear flow near the interface being analyzed. The method also includes determining a set of potential particle motion vectors based on the received images and dynamically ranks the likelihood that the potential tracks are correct based on track density. Track density is calculated using a plot matrix and kernel technique. The ranking is used to match particles from the successive images. The method also includes generating a velocity profile of the flow about the interface based on the particles matches and the determined location of the interface. The method is also applicable to moving and deforming interfaces.

41 Claims, 11 Drawing Sheets

OTHER PUBLICATIONS

Tsuei, L. et al. Treatment of interfaces in particle image velocimetry. Experiments in Fluids, 29, 203-214 (2000).

Grant, I. et al. Applied Optics. Method for the efficient incoherent analysis of particle image velocimetry images. 28:10, 1745-48 (1989).

Kim. Y. et al. Development of Digital Vector Velocimetry Method and Its Application to Lid Driven Rotating Flow. p. 848-52.

* cited by examiner

METHOD AND SYSTEM FOR SHEAR FLOW PROFILING

FIELD OF TECHNOLOGY

In general, the present invention relates to the field of particle velocimetry, in particular, the invention relates to using particle velocimetry to analyze a shear flow near an interface.

BACKGROUND

The region of flow close to an object is known as the boundary layer. Scientists and engineers have long sought methods of determining quantitative empirical data relating to fluid flow within the boundary layer. Scientists and engineers have used several techniques, including digital particle image velocimetery (DPIV) and digital particle tracking velocimetry (DPTV) to learn about the characteristics of fluid flows, in general. These methods, however, fail to provide robust data for fluid flow in a boundary layer or other shear flows near interfaces.

FIG. 1 is a diagram of a boundary layer profile 100. When a body moves relative to a surrounding fluid, a boundary layer exists very close to the body surface 102 as a result of the 'no-slip condition' and viscosity. Consider an object held stationary in a uniform oncoming flow with velocity U. The fluid in direct contact with the body surface 102 adheres to the surface 102 and has zero velocity. The fluid just above the surface 102 is slowed by frictional forces associated with the viscosity of the fluid. The closer the fluid is to the surface 102, the more it is slowed. The result is a thin layer where the tangential velocity, u, of the fluid increases from zero at the body surface 102 to a velocity close to U. This velocity at the outer edge of the boundary layer, "the exterior velocity," Ue, depends on the shape of the body. By definition, the boundary layer extends from the object's surface 102, y=0, to a position y=d, where the tangential velocity relative to the object's surface 102 is 0.99 Ue ("d99"), or 0.95 Ue ("d95"). The curve representing the continuous variation in tangential velocity from y=0 to y=d is commonly referred to as the boundary layer profile.

Normal velocity relative to the surface also varies from zero at the body surface 102 to some external value, Ve, generating what is known as the v-profile. A third profile, the w-profile, usually exists in the flow over three-dimensional surfaces, where w is tangential to the surface 102 and perpendicular to u.

The shapes of the boundary layer profiles above a particular position on a surface 102 depend on the shape of the body, surface 102 roughness, the upstream history of the boundary layer, the surrounding flow field and the Reynolds number. Flow in the boundary layer can be laminar or turbulent, resulting in radically different classes of profile shapes. The behavior of a body moving relative to a real fluid cannot be accurately described without an understanding of the boundary layer.

SUMMARY

The present invention relates to systems and methods for characterizing flow fields in and near a shear flow, such as boundary layer, to satisfy this long felt need in the art.

In one aspect, the invention relates to a computerized method of profiling a shear flow near an interface. The method includes receiving two successive images of a plurality of particles in the shear flow near the interface being analyzed. The method also includes determining a set of potential particle motion vectors based on the received images and dynamically ranking the likelihood that the potential motion vectors are correct based on motion vector density. Motion vectors can be, for example, tracks, displacements, or velocities. In one embodiment, the determination of motion vector density includes a plot matrix construction and kernel overlay technique. The ranking is used to select the correct motion vectors to match particles from the successive images. The method also includes generating a velocity profile of the flow about the interface based on the particles matches.

In one embodiment, the method also includes automatic digitization of the body surface and tracking its movement and deformation so that flow velocities can be determined with respect to the body surface as well as the field of view of the captured images.

In one embodiment, the interface is a body surface and the shear flow is a boundary layer at the interface. Features of the invention include the determination of the velocity profiles of the boundary layer, the comparison of the velocity profiles with existing analytical, experimental and numerical boundary layer profiles, and the determination of numerous parameters of boundary layer flow: (1) boundary layer thickness, (2) velocity at the outer edge of the boundary layer, (3) the tangential and normal velocity gradients at or close to the body surface, (4) the shear stress and skin friction on the body surface, (5) the nature of the boundary layer, whether laminar or turbulent, and (6) the tangential, spatial acceleration or deceleration of the boundary layer. In one embodiment, the invention takes multiple pairs of images to determine the variation of boundary layer parameters over time and position on the surface.

In one embodiment, the images are generated by an image capture device, such as a digital, film, or video camera. In other embodiments the images are retrieved from a storage device. The surface that the image capture device targets can be stationary or mobile with respect to the capture device field of view. One feature of the invention allows the method to take into account deformation of a surface being imaged between capture of successive images.

In another aspect, the invention relates to an apparatus for characterizing a boundary layer. The apparatus includes an image source, an image processor, and a data analysis module. The image source, for example, an image capture device or image storage device, outputs successive images of a body surface located in a flow. The image processor receives the images and detects particles within the images. The image processor then determines a set of potential particle motion vectors based on the location of the particles in the images. Motion vectors can be, for example, tracks, displacements, or velocities. The image processor matches the particles between images based on a dynamic ranking of the potential particle motion vectors. The dynamic ranking is based on motion vector density, which in one embodiment is calculated by a track-plot construction and kernel overlay technique. The data analysis module then determines the velocity of the particles in the images and generates a boundary layer profile.

The apparatus can be coupled to the body surface, or it can be located remotely. Illustrative body surfaces include, without limitation, the surfaces of airframes, projectiles, propellers, living organisms, apparel, turbine blades, surface nautical vessels, submersible nautical vehicles, chemical processing apparatus, etc. In one embodiment, the apparatus includes a processor for initiating a change to the body surface to decrease the drag on the surface based on the generated boundary layer profile. In another embodiment, the image source is an image capture device and can be mounted on a robot to track any motion of the body in order to keep the body surface in the field of view of the image capture device.

Additional features of the apparatus include, without limitation, the ability to compensate for movement of the surface without requiring movement of the image source, determine the friction of the body surface based on the boundary layer profile, compare the boundary layer profile with theoretical boundary layer flow models, and the ability to determine the thickness of the boundary layer.

In another aspect, the invention relates to a method for characterizing a fluid flow by receiving first and second images of a plurality of particles in the fluid flow, determining a set of potential particle motion vectors based on the received images, and assigning the potential motion vectors locations in a coordinate system according to the angle and magnitude of the potential motion vector. The method also includes determining a set of actual motion vectors by iteratively i) determining a motion vector density score for each potential motion vector by transforming the coordinate system containing the potential motion vectors into a plot matrix and applying a kernel to the plot matrix; ii) ranking the potential particle motion vectors based on motion vector density, iii) selecting an actual motion vector based on the ranking, and iv) eliminating redundant potential motion vectors based on the selection of the actual motion vector. In addition the method includes generating a velocity profile of the flow based on the set of actual motion vectors.

BRIEF DESCRIPTION OF THE DRAWINGS

The foregoing discussion will be understood more readily from the following detailed description of the invention with reference to the following drawings.

FIGS. 4B–4F illustrate, in graphic form, the steps carried out in the method FIG. 4A.

DESCRIPTION

The systems and methods described herein are described specifically in relation to the characterization of boundary layers. As is known in the art, boundary layers are one specific form of a shear flow that arises near a body surface. The systems and methods can apply to the characterization of other forms of shear flows that arise as a result of fluid flows near other forms of interfaces, such as the interface between two fluids. The systems and methods can also be used to analyze flow fields that do not include interfaces. In such cases, one edge of an analyzed image, for example, is considered to be an interface.

Figure 1:
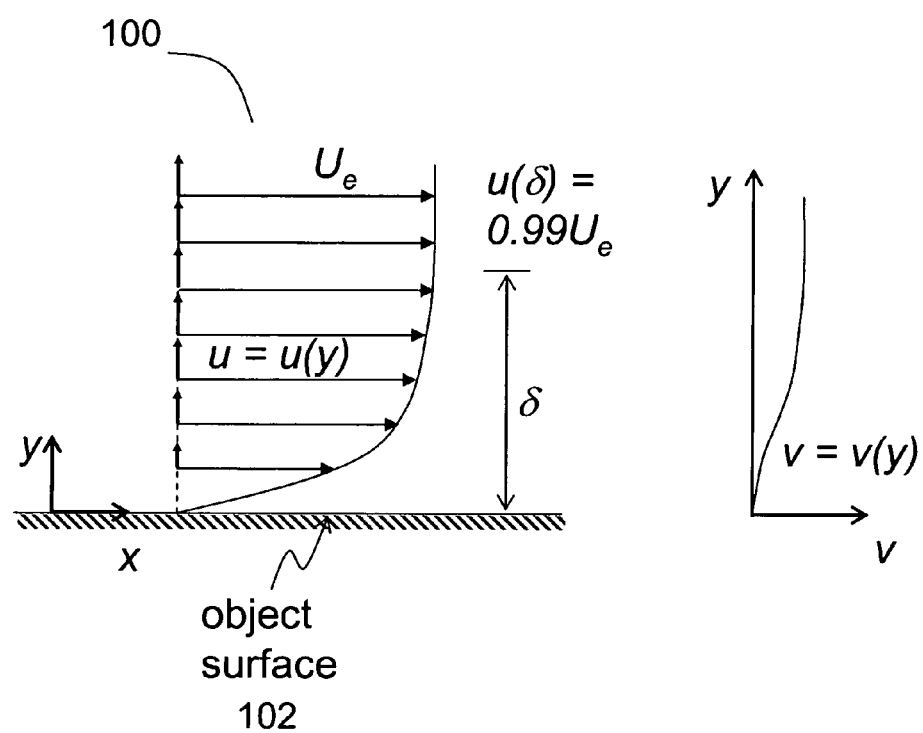
FIG. 1 is an illustrative boundary layer profile.
Figure 2:
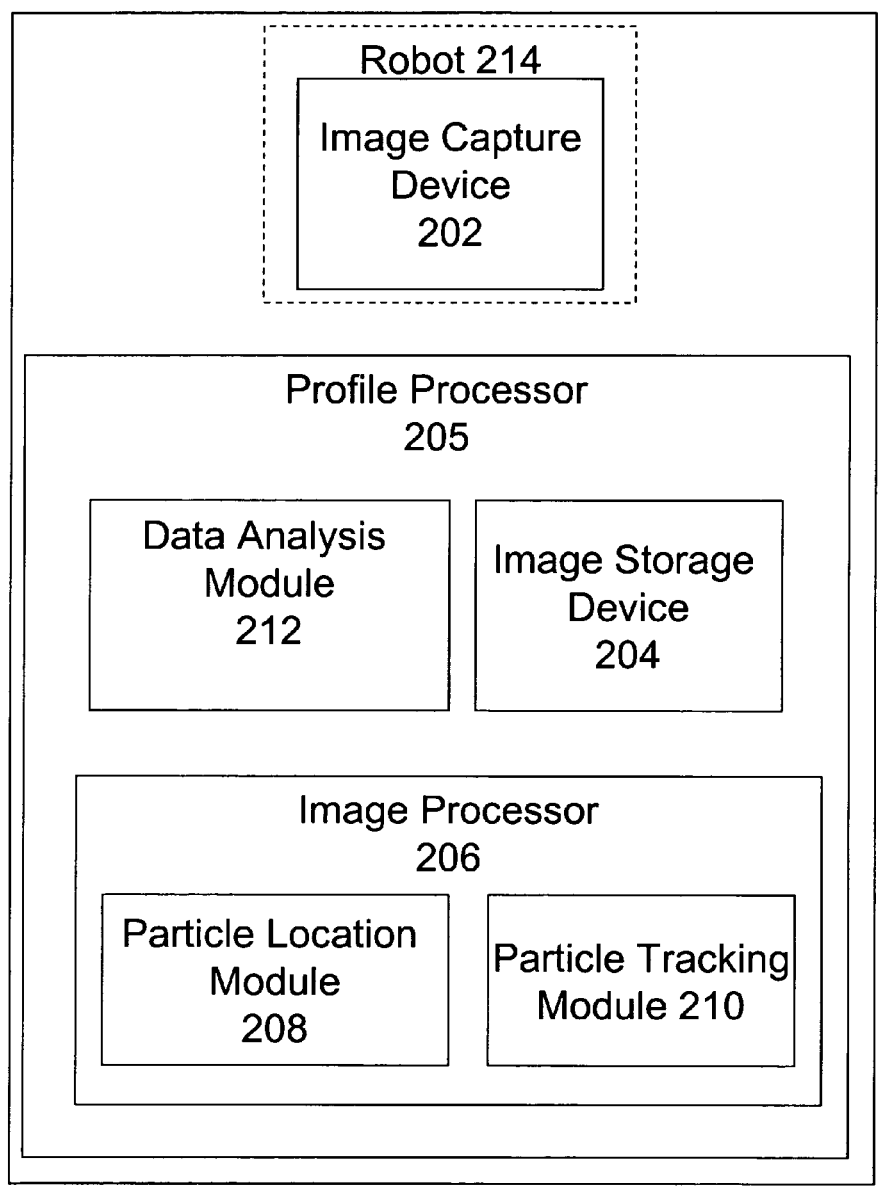
FIG. 2 is a high-level block diagram of a system for characterizing a boundary layer near a body surface according to an illustrative embodiment of the invention.

FIG. 2 is a high-level block diagram of a system for characterizing a boundary layer near a body surface ("system") 200. The system 200 includes an image source, such as an image capture device 202 and/or an image storage device 204, and a profile processor 205. The image capture device 202 captures images of a surface of a body and a surrounding fluid flow. The fluid flow is visualized by identifying particles moving passively through the flow. In the alternative, or in addition, the system 200 includes an image storage device 204, which stores in a memory, for example on an electric, magnetic, or optical storage medium, images of a surface and particles in the surrounding fluid flow. The image storage device can be part of the profile processor 205 or it can be separate from and in communication with the profile processor 205. The profile processor 205 includes an image processor 206 for analyzing the images captured by the image capture device 202 or stored on the image storage device 204. The image processor 206 further includes a particle location module 208 and a particle tracking module 210. The profile processor 205 also includes a data analysis module 212.

The profile processor 205 and its constituent modules, the particle location module 208, the particle tracking module 210, and the data analysis module 212, can be implemented as hardware, for example as an ASIC, DSP, or other form of integrated circuit. Similarly, the profile processor 205 can be implemented in software operating on a general or special purpose computing device. In a further implementation, the profile processor 205 is implemented in a combination of hardware and software. The modules can be implemented as stand alone modules, or one or more modules can be integrated together. In operation, the modules of the profile processor 205, the image capture device 202, and/or the image storage device 204 interoperate to implement a method, for example, the method described in FIGS. 3–4, to generate & characterize a boundary layer profile.

In a further embodiment, the image capture device 202 is mounted on a robot 214. In scenarios in which the body being imaged moves, the image processor 206 determines the change in location of the body and provides instructions to the robot 214 to track the movement of the body such that the body surface remains in the field of view of the image capture device 202 as often as possible.

Characterizing a boundary layer includes three general steps: particle location, particle matching, and profile generation.

Figure 3A:
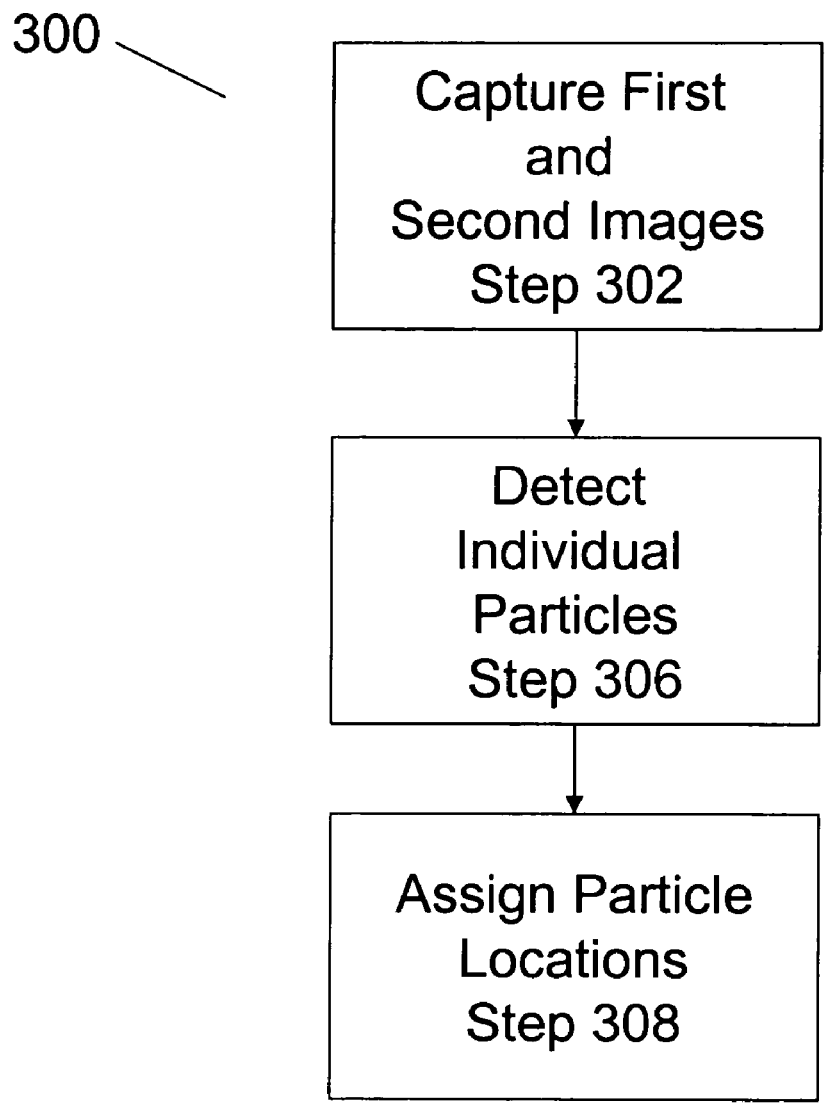
FIG. 3A is a flow chart of an illustrative method for particle location according to an illustrative embodiment of the invention.
Figure 3B:
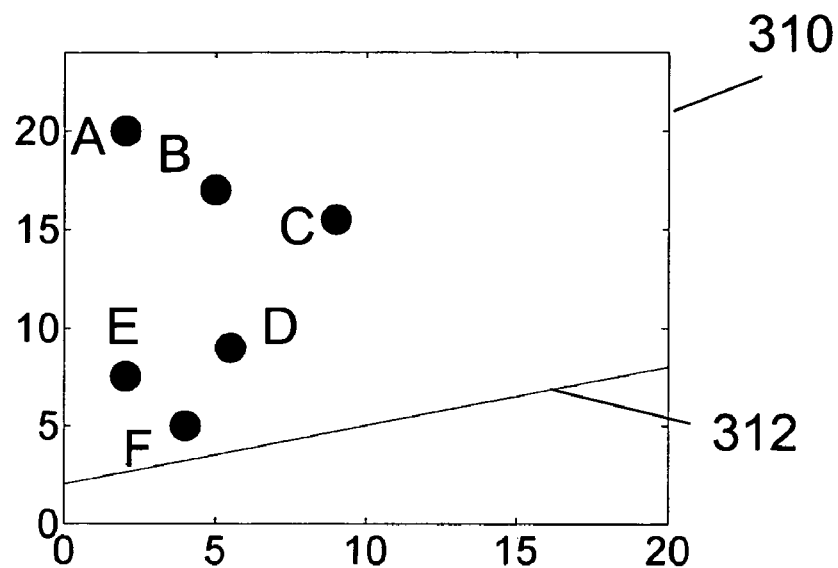
FIGS. 3B–3D illustrate, in graphic form, the steps carried out in the method of FIG. 3A.
Figure 3C:
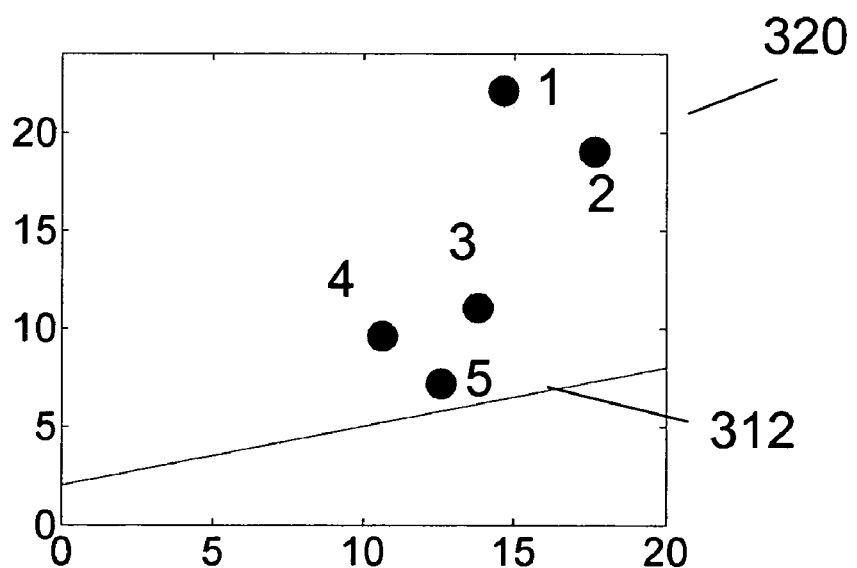

FIG. 3A is a flow chart of an illustrative method for particle location 300, as may be carried out by the particle location module 208. The illustrative particle location method 300 will be understood more clearly with reference to FIGS. 3B–3D which illustrate, in graphic form, the steps carried out in the method 300.

Particle location determination begins with capturing (step 302), for example by the image capture device 202, first and second images 310 and 320 (FIG. 3B) (FIG. 3C) of a fluid flow near a surface 312, separated by a time, dt. In one embodiment, the image capture device 202 is a digital camera, preferably having a high resolution. In other embodiments, the image capture device 202 is a film camera, video camera, or any other image capture device having sufficient resolution to discern small particles. If the image capture device 202 does not produce digital images, the images 310 and 320 are digitized. The surface 312 and particles in the surrounding fluid being analyzed may be illuminated, for example, using a laser or a strobe.

Once the images 310 and 320 are in digital format, the particle location module 208 detects individual particles within each image 310 and 320 (step 306). Particle detection (step 306), in one embodiment, includes the determination and removal of variable image glare resulting from illumination of the body surface 312. Once glare is removed, the particle location module 208 applies standard image processing techniques, for example, applying a brightness intensity filter and blob analysis, to identify particles (step 306) from the background and near the surface in each image 310 and 320. For example the first image 310 includes particles A–F. The second image 320 includes particles 1–5. In these illustrative computer generated flow images the particles D, E, and F have moved to the positions labeled as particles 3, 4, and 5, respectively. Particles A and B have moved to 1 and 2. A small amount of random error has been added to simulate real experimental data. Particle C moves out of the field of view. For simplicity, in this example the body surface is stationary and not curved.

Figure 3D:
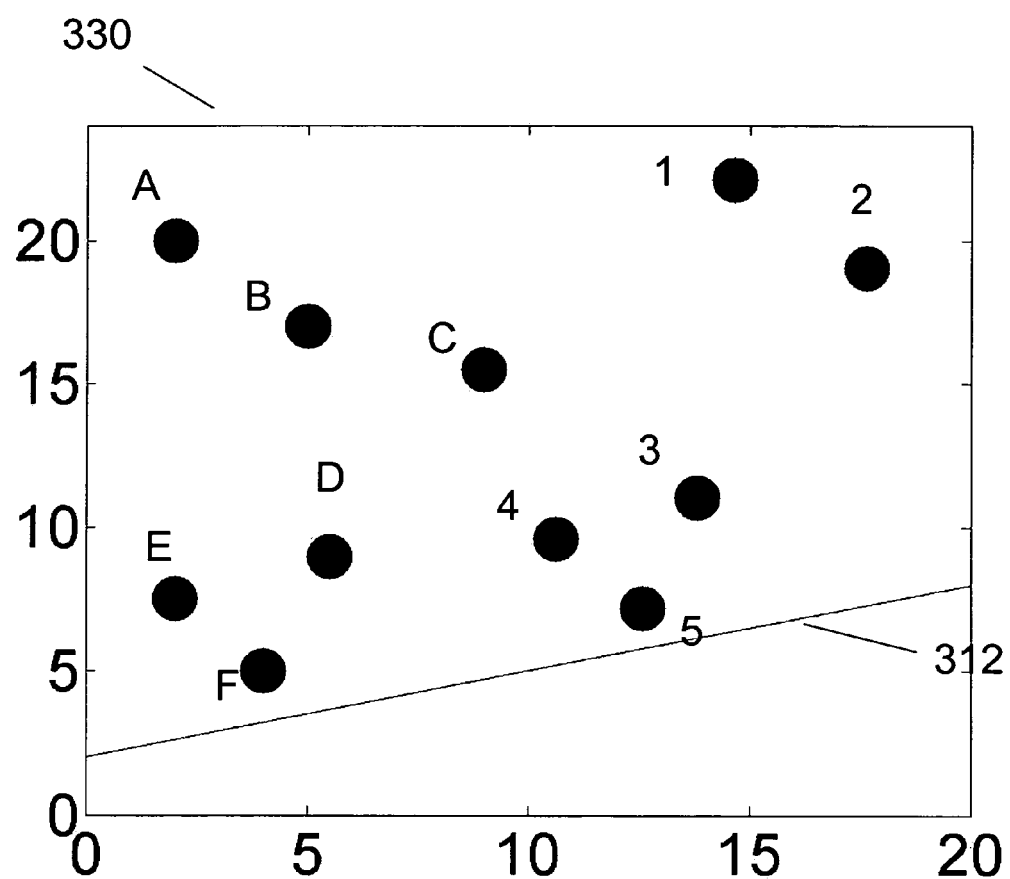

Once the particle location module 208 detects the particles (Step 306), the particle location module 208 assigns each particle A–F and 1–5 a location ($X_{fov}$, $Y_{fov}$) within the coordinate system of the image capture device 202 field of view 330 as depicted in FIG. 3D (step 308). In one embodiment, the particle location module 208 also detects the surface 312 and stores the coordinates of the surface with respect to the field of view 330. In a further implementation, after the particle location module 208 assigns locations to the particles A–F and 1–5 and the surface 312, the profile processor 205 saves the location data and deletes the images 310 and 320 from memory to save memory resources.

Figure 4A:
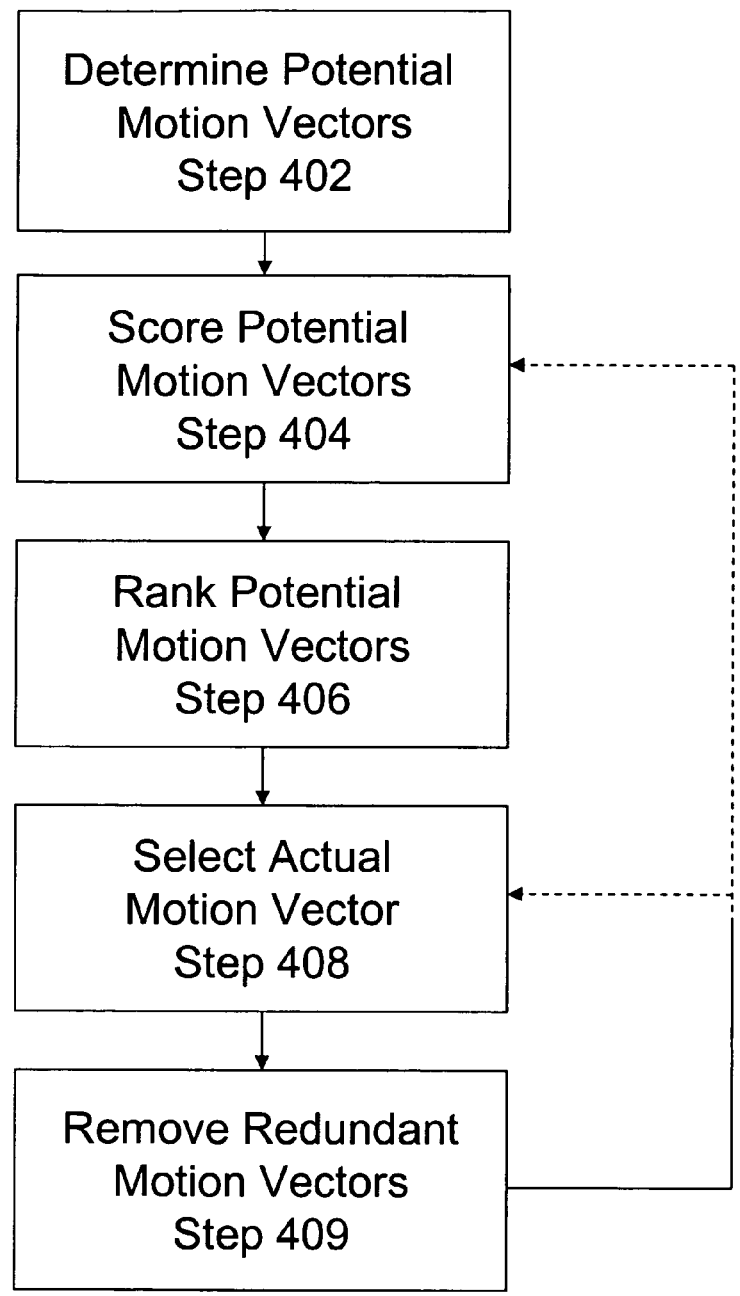
FIG. 4A is a flow chart of a method of matching particles according to an illustrative embodiment of the invention.

FIG. 4A depicts an illustrative method 400 of matching particles from the second image 320 (1–5) to the first image 310 (A–F), as carried out, for example by the particle tracking module 210. FIGS. 4B–4F graphically depict the matching analysis steps for illustrative purposes.

Figure 4B:
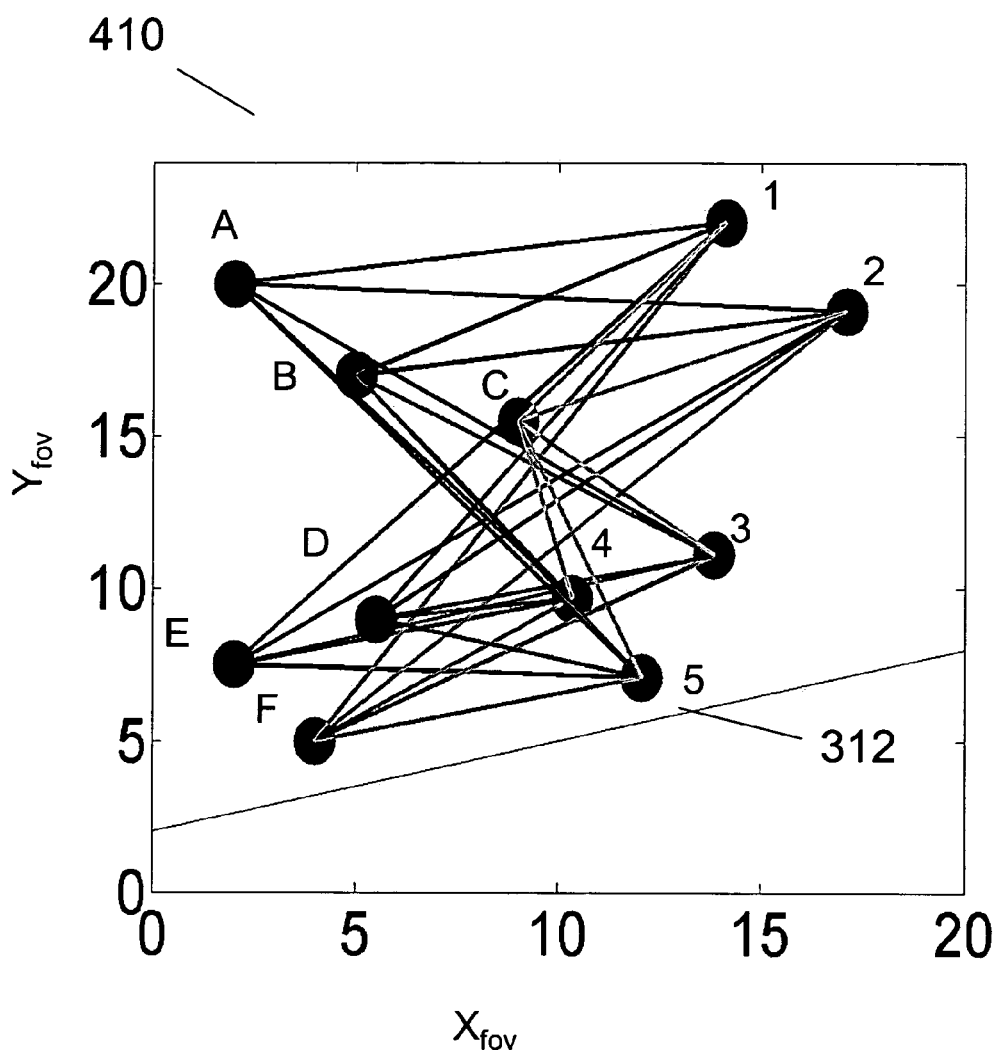

After the particle location module 208 assigns locations to the particles A–F and 1–5, the particle tracking module 210 determines a set of potential motion vectors (step 402), which, if applied to the particles A–F in the first image 310, would result in the second image 320. The motion vectors can be, for example, particle tracks, particle displacements, or particle velocities. For simplicity sake, the remainder of the method will be described assuming that the motion vector utilized is a track. FIG. 4B is a plot 410 of the particles A–F and 1–5 from the first image 310 and second image 320 connected by the set of possible tracks A1–F5 (designated by start and end location, i.e., track A1 refers to a track from particle A to particle 1).

Figure 4C:
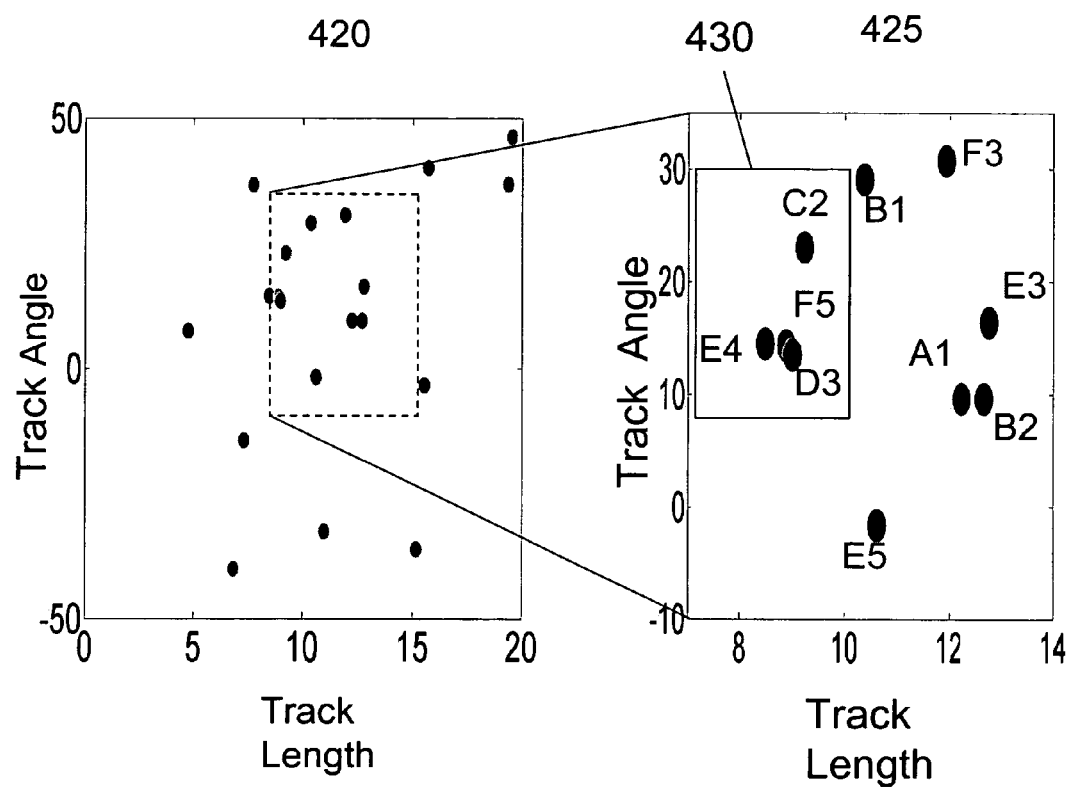

FIG. 4C includes a "track plot" 420 of the possible tracks A1–F5, and a close-up 425 of one area of interest. The x-axis of the track plot 420 corresponds to track length and the y-axis of the track plot 420 corresponds to track angle. In this way, each data point on the track plot 420 represents an individual track A1–F5. The close-up 425 includes an area of the track plot 420 that includes a higher density of potential tracks A1–F5.

A track plot 420 typically shows considerable scatter since most of the possible tracks A1–F5 are erroneous and the track angles and lengths land randomly on the plot. However, the tracks of groups of particles traveling at nearly the same velocity, that is, having nearly the same track angle and length (as would be expected in a continuous flow field, particularly at distances equidistant from a surface), land near each other on the track plot 420. That is, clusters of tracks appear on the track plot 420 for tracks representing the actual particle tracks.

Figures 4D, 4E, 4F:
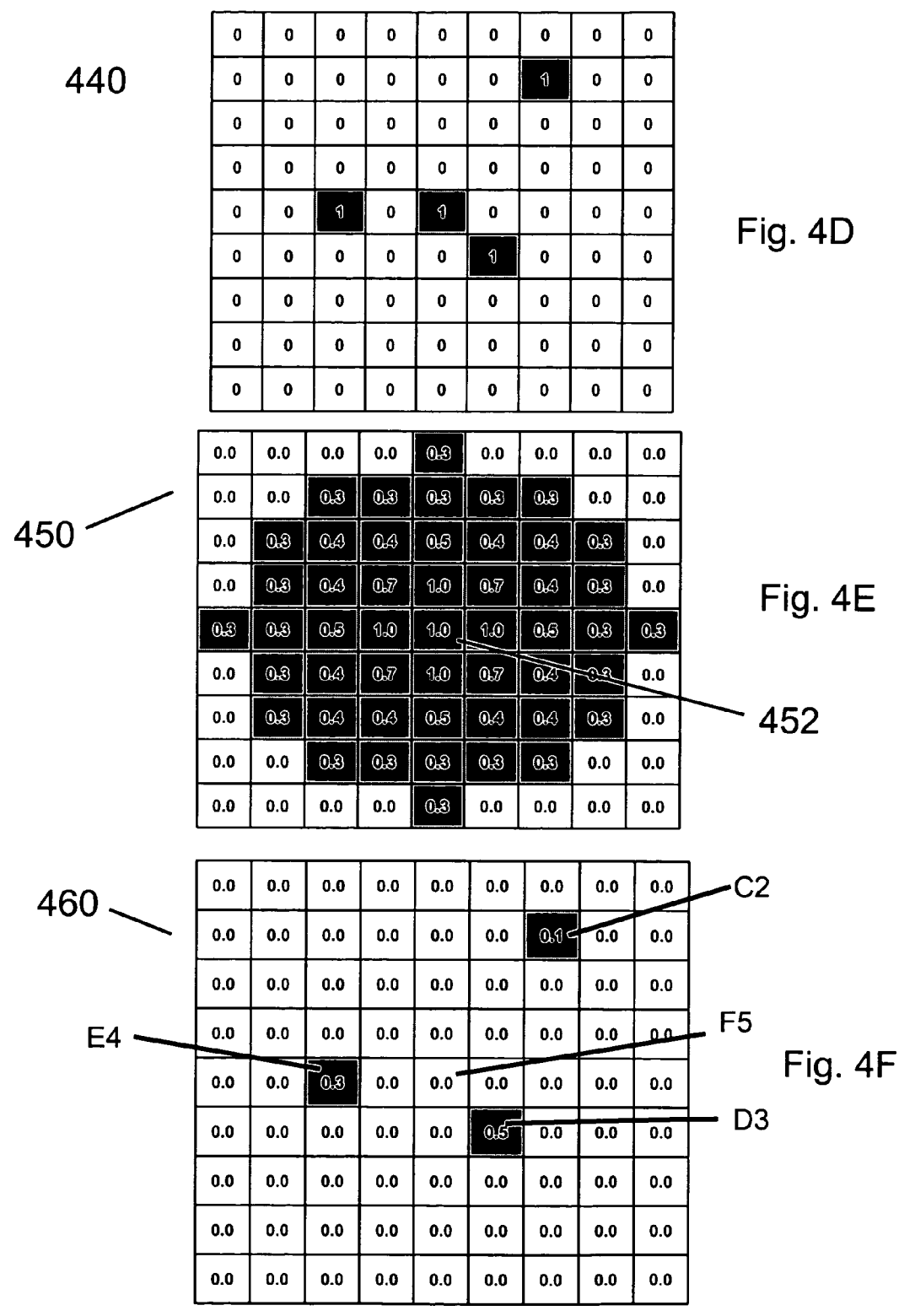

Next, the particle tracking module 210 scores (step 404) the potential tracks A1–F5 to determine the actual tracks. The particle tracking module 210 scores each potential track A1–F5 based on the density of other potential tracks A1–F5 surrounding it. In one embodiment, to determine the score of each potential track A1–F5 on the track plot 420, the particle tracking module 210 digitizes the track plot 420. The particle tracking module 210 scales the track plot 420, for example, to a 1,000 by 1,000 plot matrix 440, though the size of the matrix can be set to other sizes depending on a user's desired resolution in the analog to digital transformation of the track plot 420. FIG. 4D illustrates a partial plot matrix 440 corresponding to a portion 430 of the track plot 420. Each plot matrix 440 entry corresponds to an angle/length region on the track plot 420. The particle tracking module 210 further assigns each plot matrix 440 entry a value equal to the number of potential tracks A1–F5 that fall within the location on the track plot 420 corresponding to the plot matrix 440 entry. Conceptually, if one were to divide the track plot 420 into a grid, the value of each plot matrix 440 entry would be equal to the number of potential tracks A1–F5 falling within a particular grid square to which the matrix entry corresponds. For example, the shaded grid squares in the plot matrix 440 have values of 1, corresponding to potential tracks C2, D3, E4, and F5 seen in the portion 430 of the track plot 425.

FIG. 4E is an illustrative kernel 450 generated by the particle tracking module 210. The kernel 450 is a matrix smaller than the digitized track plot 420 with dimensions equal to, for example, the average distance between potential tracks A1–F5 on the digitized track plot 420. Potential tracks A1–F5 that fall within a circle with a diameter on the order of such a distance are more likely candidates for the actual tracks. The entries in the kernel 450 are equal to $1/R_{ij}$, where $R_{ij}$ for any entry (row i, column j) is the distance from the center 452 entry of the kernel 450 to each entry (i.e. $\sqrt{i^2+j^2}$ where i and j =0 at the center of the matrix). In addition, all the entries outside a circle circumscribed by the outline of the kernel 450 are set to zero. Basically, the kernel 450 has a circular pattern of entries in which the values of entries increase from zero to very large as you move from the edge of the kernel toward the center 452. The center 452 entry of the kernel 450 is assigned an R value of approximately ¼ to approximately 1.4, and therefore the 1/R value of the center 452 entry is approximately 0.7 to approximately 4. In one implementation, the center 452 1/R value is set to 1.

The particle tracking module 210 then 'overlays' the kernel 450 onto the entries in the plot matrix 440 that have one or more potential tracks A1–F5 associated with it, one at a time, centering the kernel 450 on each entry. The particle tracking module 210 assigns each potential track A1–F5 a density score equal to the sum of the products of the overlapping kernel 450 and plot matrix 440 entries. For these calculations, in one implementation, the value of the plot matrix 440 entry over which the kernel 450 is centered is reduced by 1 so that a particle track does not contribute to its own score. This prevents giving high density scores to tracks when two incorrect tracks randomly land near each other on the track plot. The particle tracking module 210, based on the above process, assigns potential tracks A1–F5 that have several other potential tracks A1–F5 located nearby high density scores, whereas the particle tracking module 210 assigns much lower scores to isolated potential tracks (e.g., E5, FIG. 4C).

FIG. 4F is an illustration of one such overlay 460. In the overlay 460, the kernel 450 has been centered on potential track F5. Based on such an overlay, F5 would be granted a density score of 0.9. The score is the sum of contributions provided by C2(0.1), D3(0.5), and E4(0.3). This conversion of the potential track scoring problem into one of image processing and matrix manipulation (i.e. utilizing the plot matrix 440, and kernel 450) increases the speed of reaching a density score for each potential track in contrast to determining nearest neighbors for each potential track by sorting actual distances between each and every potential track and then calculating density, though such a method would also be effective.

After the potential tracks are scored, the particle tracking module 210 ranks (step 406) the potential tracks by their respective density scores. In an iterative fashion, the particle tracking module 210 selects the highest ranked potential track as an actual track (step 408), removes redundant remaining potential tracks A1–F5 (step 409)(e.g., if the top ranking potential track is track B3, all other potential tracks including particles B or 3 are removed from contention); and moves on to select the next highest ranking track of the remaining potential tracks A1–F5 (step 408). In one implementation, the particle tracking module 210 rescores (step 404) the remaining viable potential tracks before they are re-ranked to limit the effect of already determined false tracks. In another embodiment, the particle tracking module 210 removes from contention any potential track A1–F5 having an initial density score lower than a user defined threshold (e.g., 10% of the average density score) before any true tracks are selected.

In one implementation, the particle tracking module 210 takes into account the shape of the surface in matching the particles from the first image 310 to the second image 320. For example, if the surface is significantly curved, the particle tracking module 210 determines the track angle with respect to the surface since the motion of particles in the boundary layer near a surface is influenced by that surface. Therefore, particles some distance away from each other, but at a similar distance from the surface, may trace out similar tracks with respect to the surface. Unless track angle is determined with respect to the curved surface, however, the tracks traced out by these particles with respect to the field of view of the image will be angularly dissimilar. If particle density is high enough, the step of determining the track angle with respect to the surface can be skipped to reduce processing time.

In a further embodiment, the number of tracks the particle tracking module 210 analyzes at any one time is reduced by dividing each image 310 and 320 into a number of slices that run parallel to the surface 312. Slices may, but need not overlap. Slice dimensions preferably are large enough to encompass greater than about 10 particles per slice, and slices including up to several hundred particles or more will improve performance. Preferably, the slices used to divide the second image 320 are thicker than those used to slice the first image 310. The increase in thickness should be the maximum distance a particle would be expected to travel perpendicular to the interface, $dy_{max}$, with respect to the interface. This value is usually very small near interfaces. Therefore, one need not know very much about the flow at all in order to select an appropriate slice size, especially if the slice thickness in the first image 310 is at least 2–3 times larger than $dy_{max}$.

The particle tracking module 210 matches particles from the slices in the first image 310, to the corresponding slices in the second image 320. In a further embodiment, the individual slices are further sectioned when particle densities are high. Slicing the images 310 and 320 reduces processing time and limits the number of false tracks analyzed, thereby reducing the potential for introducing error into the final results.

After the particle tracking module 210 matches particles from the first image 310 to particles in the second image 320, the data analysis module 212 characterizes the boundary layer about the surface 312. The data analysis module 212, depending on the particular implementation, generalizes the velocity of the flow field, determines the velocity profiles of the boundary layer, compares the velocity profiles with existing analytical, experimental and numerical boundary layer profiles and determines numerous parameters of the boundary layer flow including: (1) boundary layer thickness, (2) velocity at the outer edge of the boundary layer, (3) the tangential and normal velocity gradients at or close to the body surface, (4) the shear stress and skin friction on the body surface, (5) the nature of the boundary layer, whether laminar or turbulent, and (6) the tangential, spatial acceleration or deceleration of the boundary layer. In one embodiment, the system 200 acquires and analyzes multiple pairs of images to determine the variation of boundary layer parameters over time and position on the surface.

Figure 5:
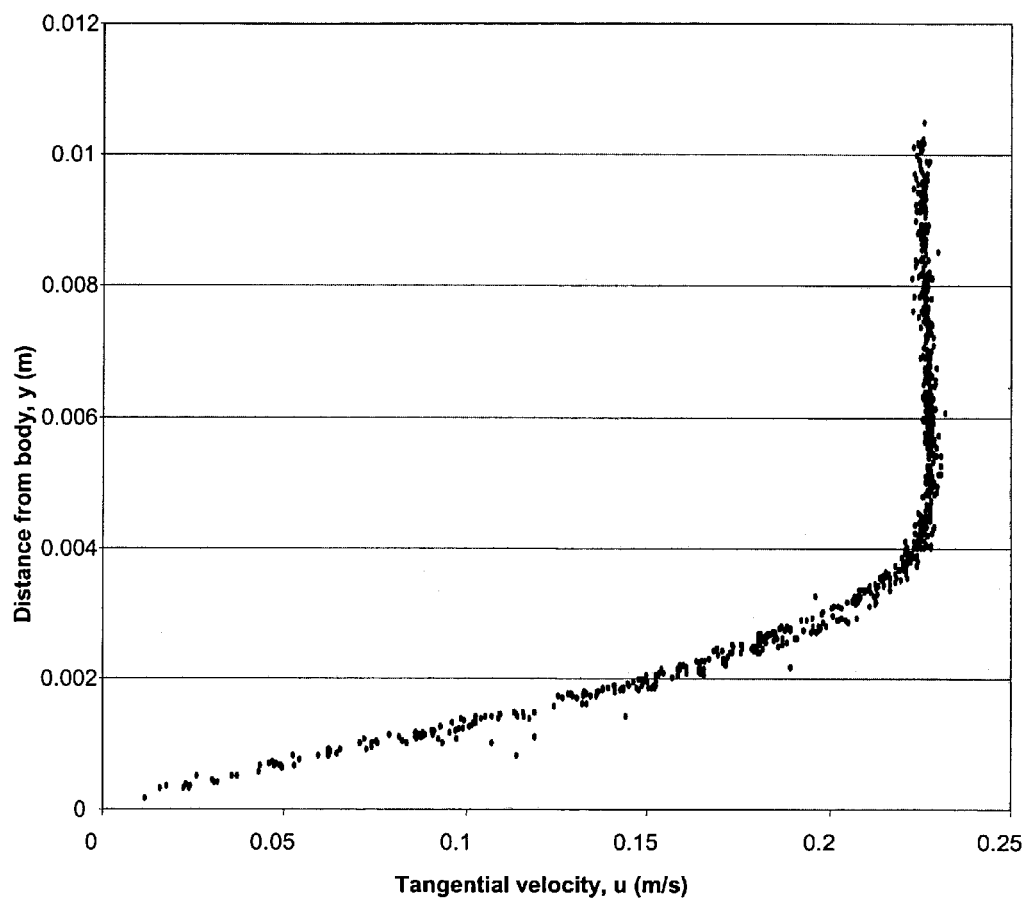
FIG. 5 is an illustrative tangential boundary layer profile as generated according to an illustrative embodiment of the invention.

FIG. 5 is an illustrative tangential boundary layer profile generated according to one embodiment of the invention. The data analysis module 212 begins the boundary layer characterization by plotting the velocities corresponding to the actual particle tracks near the surface 312 to generate a boundary layer profile. Particle velocity is determined by dividing the track length by the time between image exposures, dt. In one embodiment, the data analysis module 212 generalizes the flow field by plotting each velocity as a vector beginning at the corresponding track's midpoint, having the same direction as the track and a length proportional to the velocity. The data analysis module 212 interpolates these vectors to produce a rectangular grid of velocities for calculation of other hydrodynamic properties of the flow, such as vorticity. In one embodiment, the data analysis module 212 computes velocity components tangential and normal to the surface from each track, and plots each component separately vs. the distance of the track midpoint from the surface (or the average surface in cases of a moving surface). The resulting plots are the boundary layer profiles.

The data analysis module 212 further analyzes the data to determine the thickness of the boundary layer. A typical tangential boundary layer profile shows a steep increase in tangential velocity as one moves a short distance from the body surface (FIG. 5). The tangential velocity reaches some maximum (the exterior velocity "Ue") that remains somewhat constant as one moves farther from the body. Therefore, on the tangential profile plot generated above, since there are usually a large number of particles moving at Ue outside the boundary layer, there is usually a highly concentrated vertical strip of points at Ue extending upward in distance from the body surface starting at the boundary layer thickness (FIG. 5). The data analysis module 212 locates this strip of concentrated data points by searching for the vertical strip on the profile plot with the most data points, and then calculates Ue from the average tangential velocity of the data points in the strip. The thickness of the boundary layer is defined as the distance from the surface to the point at with tangential velocity is equal to 99% Ue ("d99"). In an alternative embodiment, the thickness of the boundary layer is based on the distance from the surface where the tangential velocity is 95% of Ue ("d95"). The data analysis module 212 determines d99 and/or d95.

In one embodiment, the data analysis module 212 removes additional spurious data points based on the determination of Ue and the boundary layer thickness. For example, all velocities greater than Ue within the boundary layer are most likely the result of tracking errors. Similarly, velocities less than about 80% of Ue and greater than about 120% of Ue at distances beyond the boundary layer are also likely to be erroneous. The exact percentages can be optimized by determining the standard deviation in the data used to calculate Ue and choosing values representing an envelope of 1–2 standard deviations. In one embodiment, the data analysis module 212 removes data points above a line, $L_1$, running from the point $(u,y)=(0,y_{int})$ to the point $(u,y)=(80\%*Ue,d)$ where u is tangential velocity, d is d99 (preferred) or d95, and $y_{int}$ is the y-intercept of the line, $L_1$, set by a user defined percentage of d. In one embodiment, the data analysis module also removes data points below the line drawn from $(u,y)=(80\%*Ue,0)$ to $(u,y)=(120\%*Ue,d)$. Once again, the percentages can be set by the user to enhance the performance based on the quality of the user's data. In one embodiment, the data analysis module filters out additional erroneous data points using the normal velocity profile, removing data points of normal velocities higher and lower than user set percentages of Ue. Since every data point on the normal profile has a corresponding data point on the tangential profile, the data analysis module 212 removes erroneous data points determined by the several methods above from both the tangential and normal velocity plots to improve further analysis.

The nature of the boundary layer (i.e. laminar or turbulent), is an important piece of information for industry and academic research. The nature of the boundary layer can drastically affect overall drag, vehicle performance, chemical reactions and chemical diffusion near surfaces and other interfaces. Laminar and turbulent boundary layer profiles have significantly different curve shapes.

Several analytical, numerical, and experimental methods have been used by scientists to determine standard boundary layer velocity profiles for laminar and turbulent boundary layers over simple surface geometries. Experimentally measured boundary layer profiles can be loosely classified on the basis of their resemblance to these known profiles. Specifically these known boundary layer profiles include the laminar boundary layer solution of Blasius, the accelerating and decelerating laminar boundary layer solution of Falkner and Skan, and the experimentally determined Law of the Wall, for turbulent boundary layers. These known profiles apply to specific flows over flat or angled surfaces, nevertheless experimentally measured boundary layer profiles for other object geometries often show sufficient similarities to allow classification.

The data analysis module 212 compares the measured boundary layer profiles against the known boundary layer profiles—Blasius, Falkner-Skan, and the Law of the Wall to determine which theoretical boundary layer profile most nearly resembles the generated velocity profile. In one embodiment, the data analysis module 212 fits the generated profile to the known profiles using the method of least squares. To speed the fitting, the data analysis module 212 uses the determined values of Ue and d99 or d95, which are variables in the theoretical equations. Since these quantities have already been determined by the data analysis module 212, there are fewer variables in the fitting process, thus reducing the computational time necessary to find a fit. To classify the boundary layer profile shape, the goodness of fit of each of the three known boundary layer profiles to the actual data is rated. For comparison, this rating is determined by dividing the sum of the squared differences, i.e. deviations, of the actual data from each attempted fit by the number of experimental profile data points. The fit with the lowest rating of deviation is considered the known profile that best describes the given boundary layer profile. This allows the data analysis module 212 to make conclusions about the nature of the boundary layer—whether it is laminar or turbulent, accelerating or decelerating.

In addition to the known profiles, the data analysis module 212 fits a straight line to the tangential velocity profile in the region closest to the body. The data analysis module 212 uses the reciprocal slope of this line as the velocity gradient at the surface and uses the velocity gradient to determine shear stress at the surface, which is known as wall shear stress. The data analysis module calculates and scales the sum of the squared differences for this linear fit for an additional level of boundary layer type determination. This can be used to determine which of the theoretical profiles best fits the lower regions of the boundary layer.

The gradient in the velocity of flow near a surface 312 arises from friction. The surface 312 is slowing down the flow near it by shear forces opposing the bulk flow. The data analysis module 212 determines the friction of the surface from the wall shear stress calculated above, or from that of the known profile fit of the boundary layer. If boundary layer profiles are determined at several positions along the body surface 312, the data analysis module 212, in one embodiment, sums this data over the body and calculates the total skin friction on the body.

In one embodiment, the data analysis module 212 performs the linear, Blasius and Law of the Wall fits twice. The first fit constrains the fit curve to intersect with the origin of the plot. The second fit allows the y-intercept of the fit curve to vary. The second fit allows for the possibility that slight errors were made in determining the exact location of the body surface 312 due to glare or to poor data. The sum of squared differences and the limits of expected error can then be used to determine if such errors are a factor. If so the surface 312 location can simply be shifted by the amount suggested by the fit y-intercept.

The data analysis module 212 outputs data files including the profile plots, and a parameter file that lists a number of parameters related to the boundary layer profile analysis such as Ue, boundary layer thickness, wall shear stress, ratings of the known profile fits, and other variables needed to reconstruct the known profiles that were fit to the data. In one implementation, parameters are also included that indicate whether a particular curve fit failed to minimize the sum of squared differences (indicating an unsatisfactory fit). Common fluid parameters such as the Reynolds number and coefficients of friction can also be included in the parameter data file. The outputted data files can be opened, for example, in a conventional spreadsheet application, such as Microsoft Excel™, or accessed by user developed code for further manipulation. The filtered boundary layer profile data can also saved in spreadsheet form.

Figure 6A:
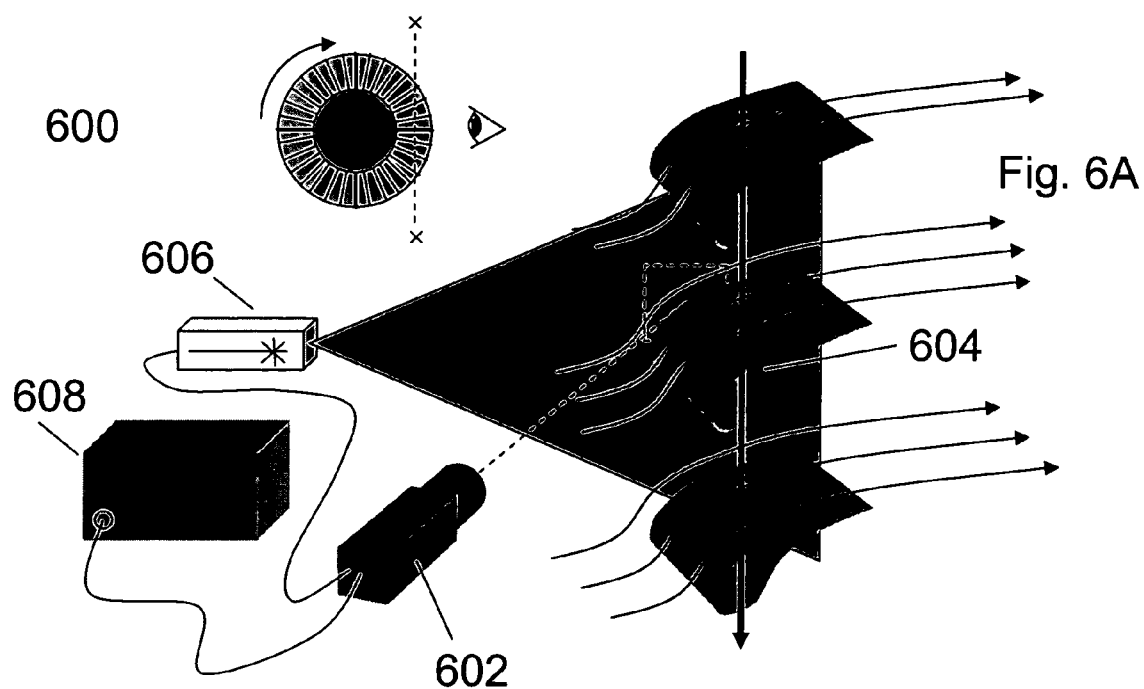
FIGS. 6A–6B are depictions of two illustrative boundary layer profiling system installations.
Figure 6B:
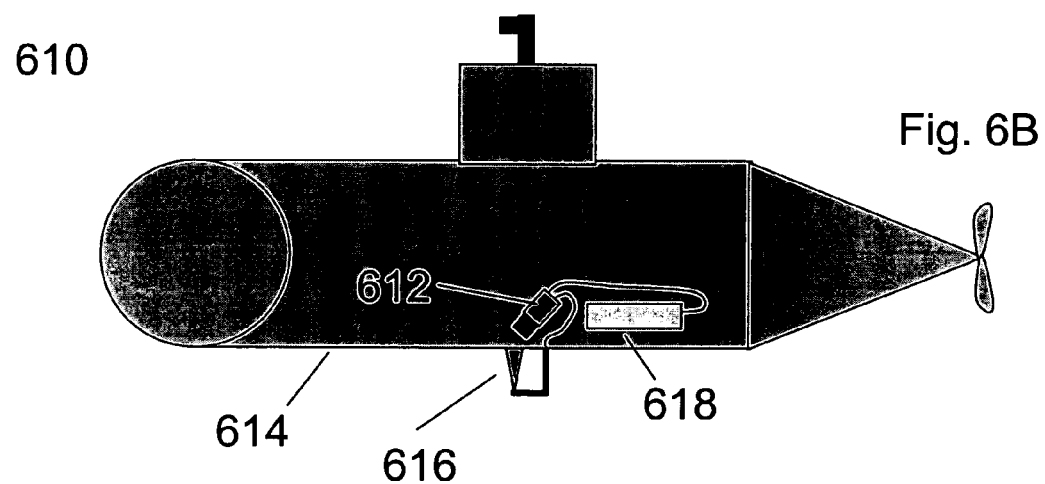

FIGS. 6A–6B are illustrative installations 600 and 610 of the boundary layer characterization system. In each installation 600 and 610, an image capture device 602 and 612, with a synchronized light source 606 and 616, is positioned a distance from a surface, such as a turbine blade 604 or the hull of a submersible vehicle 614. The image capture devices 602 and 612 are in communication with the profile processors 608 and 618 of the installations 600 and 610.

In the case of the turbine blade, the image capture device 602 is mounted separately from the turbine blade 604. The turbine blade installation 600 illustrates the use of the boundary layer characterization system 200 in the design and testing phases of the product development process. Developers can gather data on the boundary layer generated by the turbine blade 604 in a wind tunnel, for example. Collected data can be used to determine alterations to the material composition or surface characteristics of the turbine blade 604 before full production begins.

The submersible installation 610, demonstrates one application of the boundary layer characterization system 200 in the field. In the case of the submersible vehicle 614, the image capture device 612 is mounted directly to the hull of the vehicle 614. During navigation, the boundary layer characterization system 200 monitors the friction on the vehicle's 614 surface in real time. Collected data can be utilized to determine a preferred hull shape or hull texture based on the particular underwater environment and desired operational parameters in which the vehicle 614 is navigating. The hull shape and or texture can then be dynamically altered in response to the collected data.

One skilled in the art would recognize that the turbine blade 604 and submersible vehicle 614 are merely illustrative examples of products and vessels for which the boundary layer characterization system may apply. Additional surfaces, without limitation, include surfaces of swimsuits, aircraft, projectiles, living organisms, ground vehicles, surface vessels, mixing vessels, and chemical apparatus.

The invention may be embodied in other specific forms without departing form the spirit or essential characteristics thereof. The forgoing embodiments are therefore to be considered in all respects illustrative, rather than limiting of the invention.

What is claimed is:

1. A computerized method of profiling a shear flow near an interface comprising:
   receiving first and second images of a plurality of particles in the shear flow near the interface wherein the images are generated at successive time instants;
   determining a set of potential particle motion vectors based on the received images;
   dynamically ranking the potential particle motion vectors based on motion vector density;
   matching particles in the first image to particles in the second image based on the dynamic ranking; and
   generating a velocity profile about the interface based on the particle matching.

2. The method of claim 1 wherein the motion vector is one of a track, a velocity, and a displacement.

3. The method claim 1 wherein dynamically ranking the potential motion vectors further comprises assigning the potential motion vectors locations in a coordinate system according to the angle and magnitude of the potential motion vector.

4. The method of claim 3 wherein the motion vector density of a potential motion vector is determined based on the location of the potential motion vector in the coordinate system in relation to the locations of other potential motion vectors in the coordinate system.

5. The method of claim 4 wherein the motion vector density is calculated by transforming the coordinate system containing the potential motion vectors into a plot matrix and applying a kernel to the plot matrix.

6. The method of claim 1 wherein the matching of particles further comprises selecting a high ranked potential motion vector as an actual motion vector.

7. The method of claim 6 wherein the matching of particles further comprises removing redundant potential motion vectors from consideration based upon the selection of an actual motion vector.

8. The method of claim 7 wherein the dynamic ranking further comprises recalculating a motion vector density after the removal of redundant potential motion vectors.

9. The method of claim 1 wherein the interface is a body surface.

10. The method of claim 9 further comprising determining shear stress on the body surface based on the velocity profile.

11. The method of claim 9 further comprising determining friction on the body surface based on the velocity profile.

12. The method of claim 9 wherein the images are generated by an image capture device and the body is moving relative to the image capture device.

13. The method of claim 9 wherein the body deforms between generation of the first and second images.

14. The method of claim 1 further comprising determining a boundary layer thickness.

15. The method of claim 1 further comprising comparing the velocity profile with known boundary layer profiles.

16. The method of claim 1 wherein the first and second images are obtained from a storage device.

17. An apparatus for characterization of a boundary layer:
   a. an image source outputting successive images of a body surface in a flow;
   b. an image processor in communication with the image source configured to
      i. receive the successive images output by the image source;
      ii. detect particles in the successive images;
      iii. determine a set of potential motion vectors of the detected particles based on the received images;
      iv. dynamically rank the potential motion vectors in the set based on motion vector density;
   c. a data analysis module in communication with the image processor configured to:
      i. determine the velocity of particles located in the boundary layer near the body surface based on the ranked set of potential motion vectors; and
      ii. generate a boundary layer profile.

18. The apparatus of claim 17 wherein the motion vector is one of a track, a velocity, and a displacement.

19. The apparatus of claim 17 wherein dynamically ranking the potential motion vectors further comprises assigning the potential motion vectors locations in a coordinate system according to the angle and magnitude of the potential motion vectors.

20. The apparatus of claim 19 wherein the motion vector density of a potential motion vector is determined based on the location of the potential motion vector in the coordinate system in relation to the locations of other potential motion vectors in the coordinate system.

21. The apparatus of claim 19 wherein the motion vector density is calculated by transforming the coordinate system containing the potential motion vectors into a plot matrix and applying a kernel to the plot matrix.

22. The apparatus of claim 17 wherein the matching of particles further comprises selecting a high ranked potential motion vector as an actual motion vector.

23. The apparatus of claim 22 wherein the wherein the matching of particles further comprises removing redundant potential motion vectors from consideration based upon the selection of an actual motion vector.

24. The apparatus of claim 23 wherein the dynamic ranking further comprises recalculating a motion vector density after the removal of redundant potential motion vectors.

25. The apparatus of claim 17 further comprising a processor for initiating an alteration to the body surface to decrease drag based at least in part upon the determined boundary layer profile.

26. The apparatus of claim 17 wherein the image source is coupled to the body surface.

27. The apparatus of claim 17 wherein the image source is an image capture device.

28. The apparatus of claim 27 wherein the image capture device is coupled to a robot configured to track motion of the body.

29. The apparatus of claim 17 wherein the image source is separate from and in communication with the image processor.

30. The apparatus of claim 17 wherein the image source is an image storage device.

31. The apparatus of claim 17 wherein the image processor is further configured to determine the displacement of the body surface between the capture of the subsequent images.

32. The method of claim 17 wherein the data analysis module determines at least one of the shear stress and the friction on the body surface based on the boundary layer profile.

33. The method of claim 17 wherein the data analysis module determines the thickness of the boundary layer.

34. The method of claim 17 wherein the data analysis module compares the boundary layer profile with known boundary layer profiles.

35. The apparatus of claim 17 wherein the body is a propeller blade.

36. The apparatus of claim 17 wherein the body is a turbine blade.

37. The apparatus of claim 17 wherein the body is a surface aquatic vehicle.

38. The apparatus of claim 17 wherein the body is a submersible aquatic vehicle.

39. The apparatus of claim 17 wherein the body is an airframe.

40. The apparatus of claim 17 wherein the body is a living organism.

41. A method of characterizing a fluid flow comprising:

receiving first and second images of a plurality of particles in the fluid flow wherein the images are generated at successive time instants;

determining a set of potential particle motion vectors based on the received images;

assigning the potential motion vectors locations in a coordinate system according to the angle and magnitude of the potential motion vector;

determining a set of actual motion vectors by iteratively:

i) determining a motion vector density score for each potential motion vector by transforming the coordinate system containing the potential motion vectors into a plot matrix and applying a kernel to the plot matrix;

ii) ranking the potential particle motion vectors based on motion vector density, iii) selecting an actual motion vector based on the ranking, iv) eliminating redundant potential motion vectors based on the selection of the actual motion vector; and generating a velocity field of the flow based on the set of actual motion vectors.

* * * * *